(12) United States Patent
Mosnier et al.

(10) Patent No.: US 10,314,657 B2
(45) Date of Patent: **\*Jun. 11, 2019**

(54) METHODS, SYSTEMS, AND DEVICES FOR DESIGNING AND MANUFACTURING A SPINAL ROD

(71) Applicant: Medicrea International, Rillieux-la-Pape (FR)

(72) Inventors: Thomas Mosnier, Rochetaillée sur Saône (FR); David Ryan, Collonges Au Mont d'Or (FR)

(73) Assignee: Medicrea International, Rillieux-la-Pae (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,694

(22) Filed: Jul. 18, 2018

(65) Prior Publication Data

US 2019/0046268 A1    Feb. 14, 2019

Related U.S. Application Data

(63) Continuation of application No. 15/694,227, filed on Sep. 1, 2017, now Pat. No. 10,045,824, which is a
(Continued)

(51) Int. Cl.
*G06T 7/00* (2017.01)
*A61B 34/10* (2016.01)
(Continued)

(52) U.S. Cl.
CPC .......... *A61B 34/10* (2016.02); *A61B 17/7011* (2013.01); *A61B 17/8863* (2013.01);
(Continued)

(58) Field of Classification Search
None
See application file for complete search history.

(56) References Cited

U.S. PATENT DOCUMENTS

| 5,006,984 A | 4/1991 | Steele |
| 5,163,440 A | 11/1992 | DeLuca et al. |

(Continued)

FOREIGN PATENT DOCUMENTS

| AU | 2015258176 | 12/2015 |
| AU | 2015202416 | 3/2017 |

(Continued)

OTHER PUBLICATIONS

US 9,451,972 B2, 09/2016, Lang et al. (withdrawn)
(Continued)

*Primary Examiner* — Delomia L Gilliard
(74) *Attorney, Agent, or Firm* — Knobbe, Martens, Olson & Bear, LLP

(57) ABSTRACT

According to the invention, the process includes the steps of: a) taking a sagittal preoperative x-ray of the vertebral column of the patient to be treated, extending from the cervical vertebrae to the femoral heads; b) on that x-ray, identifying points on S1, S2, T12 et C7; c) depicting, on the said x-ray, curved segments beginning at the center of the plate of S1 et going to the center of the plate of C7; e) identifying, on that x-ray, the correction(s) to be made to the vertebral column, including the identification of posterior osteotomies to make; f) pivoting portions of said x-ray relative to other portions of that x-ray, according to osteotomies to be made; g) performing, on said x-ray, a displacement of the sagittal curvature segment extending over the vertebral segment to be corrected; h) from a straight vertebral rod (TV), producing the curvature of that rod according to the shape of said sagittal curvature segment in said displacement position.

20 Claims, 5 Drawing Sheets

Related U.S. Application Data continuation of application No. 15/469,302, filed on Mar. 24, 2017, now Pat. No. 9,782,228, which is a continuation of application No. 15/024,150, filed as application No. PCT/IB2014/065150 on Oct. 8, 2014, now Pat. No. 9,693,831.

(51) Int. Cl.

| | | |
|---|---|---|
| *A61B 17/70* | (2006.01) | |
| *A61B 17/88* | (2006.01) | |
| *G06T 7/33* | (2017.01) | |
| *A61B 17/00* | (2006.01) | |
| *A61B 17/56* | (2006.01) | |

(52) U.S. Cl.
CPC ............ *G06T 7/0012* (2013.01); *G06T 7/337* (2017.01); *A61B 2017/00526* (2013.01); *A61B 2017/568* (2013.01); *A61B 2034/108* (2016.02); *G06T 2207/10116* (2013.01); *G06T 2207/30012* (2013.01); *G06T 2207/30052* (2013.01)

(56) References Cited

U.S. PATENT DOCUMENTS

| | | | |
|---|---|---|---|
| 5,224,035 | A | 6/1993 | Yamashita et al. |
| 5,251,127 | A | 10/1993 | Raab |
| 5,291,901 | A | 3/1994 | Graf |
| 5,305,203 | A | 4/1994 | Raab |
| 5,413,116 | A | 5/1995 | Radke et al. |
| 5,514,130 | A | 5/1996 | Heggeness |
| 5,748,767 | A | 5/1998 | Raab |
| 5,785,663 | A | 7/1998 | Sarvazyan |
| 6,015,409 | A | 1/2000 | Jackson |
| 6,213,958 | B1 | 4/2001 | Winder |
| 6,282,437 | B1 | 8/2001 | Franck et al. |
| 6,364,849 | B1 | 4/2002 | Wilcox |
| 6,385,475 | B1 | 5/2002 | Cinquin et al. |
| 6,409,684 | B1 | 6/2002 | Wilk |
| 6,499,488 | B1 | 12/2002 | Hunter et al. |
| 6,565,519 | B2 | 5/2003 | Benesh |
| 6,585,666 | B2 | 7/2003 | Suh et al. |
| 6,711,432 | B1 | 3/2004 | Krause et al. |
| 6,715,213 | B2 | 4/2004 | Richter |
| 6,736,930 | B1 | 9/2004 | Biscup |
| 7,338,526 | B2 | 3/2008 | Steinberg et al. |
| 7,509,183 | B2 | 3/2009 | Lin |
| 7,534,263 | B2 | 5/2009 | Burdulis |
| 7,606,613 | B2 | 10/2009 | Simon et al. |
| 7,611,522 | B2 | 11/2009 | Gorek |
| 7,618,451 | B2 | 11/2009 | Fitz et al. |
| 7,634,119 | B2 | 12/2009 | Tsougarakis et al. |
| 7,635,367 | B2 | 12/2009 | Groiso |
| 7,660,623 | B2 | 2/2010 | Hunter et al. |
| 7,674,293 | B2 | 3/2010 | Kuiper et al. |
| 7,715,602 | B2 | 5/2010 | Richard |
| 7,763,054 | B2 | 7/2010 | Clement et al. |
| 7,835,778 | B2 | 11/2010 | Foley et al. |
| 7,840,253 | B2 | 11/2010 | Tremblay et al. |
| 7,862,593 | B2 | 1/2011 | Clement et al. |
| 7,918,887 | B2 | 4/2011 | Roche |
| 7,953,471 | B2 | 5/2011 | Clayton et al. |
| 7,981,158 | B2 | 7/2011 | Fitz et al. |
| 7,996,061 | B2 | 8/2011 | Mollard et al. |
| 7,996,064 | B2 | 8/2011 | Simon et al. |
| 8,000,926 | B2 | 8/2011 | Roche et al. |
| 8,046,050 | B2 | 10/2011 | Govari et al. |
| 8,066,708 | B2 | 11/2011 | Lang et al. |
| 8,077,950 | B2 | 12/2011 | Tsougarakis et al. |
| 8,083,778 | B2 | 12/2011 | Clemet et al. |
| 8,105,330 | B2 | 1/2012 | Fitz et al. |
| 8,196,825 | B2 | 6/2012 | Turner et al. |
| 8,211,109 | B2 | 7/2012 | Groiso |
| 8,241,296 | B2 | 8/2012 | Wasielewski |
| 8,246,680 | B2 | 8/2012 | Betz et al. |
| 8,265,790 | B2 | 9/2012 | Amiot et al. |
| 8,270,253 | B1 | 9/2012 | Roche et al. |
| 8,275,594 | B2 | 9/2012 | Lin et al. |
| 8,308,772 | B2 | 11/2012 | Clemet et al. |
| 8,308,775 | B2 | 11/2012 | Clement et al. |
| 8,337,501 | B2 | 12/2012 | Fitz et al. |
| 8,372,075 | B2 | 2/2013 | Groiso |
| 8,377,073 | B2 | 2/2013 | Wasielewski |
| 8,394,142 | B2 | 3/2013 | Berg et al. |
| 8,398,681 | B2 | 3/2013 | Augostino et al. |
| 8,400,312 | B2 | 3/2013 | Hotokebuchi et al. |
| 8,414,592 | B2 | 4/2013 | Quirno |
| 8,442,621 | B2 | 5/2013 | Gorek et al. |
| 8,465,527 | B2 | 6/2013 | Clement |
| 8,494,805 | B2 | 7/2013 | Roche et al. |
| 8,506,632 | B2 | 8/2013 | Ganem et al. |
| 8,532,806 | B1 | 9/2013 | Masson |
| 8,535,337 | B2 | 9/2013 | Chang et al. |
| 8,556,983 | B2 | 10/2013 | Bojarski et al. |
| 8,588,892 | B2 | 11/2013 | Hladio et al. |
| 8,672,948 | B2 | 3/2014 | Lemaitre |
| 8,685,093 | B2 | 4/2014 | Anderson et al. |
| 8,690,888 | B2 | 4/2014 | Stein et al. |
| 8,718,820 | B2 | 5/2014 | Amiot et al. |
| 8,758,357 | B2 | 6/2014 | Frey |
| 8,777,877 | B2 | 7/2014 | Stein et al. |
| 8,784,339 | B2 | 7/2014 | Stein et al. |
| 8,801,786 | B2 | 8/2014 | Bernard et al. |
| 8,814,877 | B2 | 8/2014 | Wasielewski |
| 8,855,389 | B1 | 10/2014 | Hoffman et al. |
| 8,864,764 | B2 | 10/2014 | Groiso |
| 8,870,889 | B2 | 10/2014 | Frey |
| 8,900,316 | B2 | 12/2014 | Lenz |
| 8,911,448 | B2 | 12/2014 | Stein |
| 8,926,673 | B2 | 1/2015 | Clement et al. |
| 8,945,133 | B2 | 2/2015 | Stein et al. |
| 8,956,416 | B2 | 2/2015 | McCarthy |
| 8,974,467 | B2 | 3/2015 | Stone |
| 8,983,813 | B2 | 3/2015 | Miles et al. |
| 8,998,962 | B2 | 4/2015 | Birch |
| 9,011,418 | B2 | 4/2015 | Roche et al. |
| 9,034,037 | B2 | 5/2015 | Fiere et al. |
| 9,039,772 | B2 | 5/2015 | Park et al. |
| 9,056,017 | B2 | 6/2015 | Kotlus |
| 9,066,334 | B2 | 6/2015 | Schoenfeld et al. |
| 9,066,701 | B1 | 6/2015 | Finley et al. |
| 9,078,755 | B2 | 7/2015 | Mahfouz |
| 9,101,492 | B2 | 8/2015 | Mangione et al. |
| 9,115,998 | B2 | 8/2015 | Proulx et al. |
| 9,119,572 | B2 | 9/2015 | Gorek et al. |
| 9,119,671 | B2 | 9/2015 | Kast |
| 9,125,680 | B2 | 9/2015 | Kostrzewski et al. |
| 9,144,440 | B2 | 9/2015 | Aminian |
| 9,144,470 | B2 | 9/2015 | Proulx et al. |
| 9,168,153 | B2 | 10/2015 | Bettenga |
| 9,173,661 | B2 | 11/2015 | Metzger et al. |
| 9,180,015 | B2 | 11/2015 | Fitz et al. |
| 9,192,412 | B2 | 11/2015 | Meyrat et al. |
| 9,198,678 | B2 | 12/2015 | Frey et al. |
| 9,232,955 | B2 | 1/2016 | Bonin, Jr. et al. |
| 9,233,001 | B2 | 1/2016 | Miles et al. |
| 9,237,952 | B2 | 1/2016 | Kurtz |
| 9,248,023 | B2 | 2/2016 | Ries et al. |
| 9,250,620 | B2 | 2/2016 | Kotlus |
| 9,278,010 | B2 | 3/2016 | Gibson et al. |
| 9,283,048 | B2 | 3/2016 | Kostrzewski et al. |
| 9,289,221 | B2 | 3/2016 | Gelaude et al. |
| 9,289,270 | B2 | 3/2016 | Gielen et al. |
| 9,295,482 | B2 | 3/2016 | Fitz et al. |
| 9,295,497 | B2 | 3/2016 | Schoenfeld et al. |
| 9,295,561 | B2 | 3/2016 | Ball et al. |
| 9,301,768 | B2 | 4/2016 | Buza et al. |
| 9,308,050 | B2 | 4/2016 | Kostrzewski et al. |
| 9,308,091 | B2 | 4/2016 | Lang |
| 9,314,275 | B2 | 4/2016 | Clement et al. |
| 9,314,343 | B2 | 4/2016 | Parisi et al. |
| 9,320,547 | B2 | 4/2016 | Augostino |
| 9,320,604 | B2 | 4/2016 | Miles et al. |

(56) References Cited

U.S. PATENT DOCUMENTS

| | | |
|---|---|---|
| 9,326,780 B2 | 5/2016 | Wong et al. |
| 9,339,277 B2 | 5/2016 | Jansen et al. |
| 9,345,492 B2 | 5/2016 | Stein et al. |
| 9,358,051 B2 | 6/2016 | Sournac et al. |
| 9,358,130 B2 | 6/2016 | Livorsi et al. |
| 9,358,136 B2 | 6/2016 | Stein et al. |
| 9,364,370 B2 | 6/2016 | Kühnel |
| 9,381,085 B2 | 7/2016 | Axelson et al. |
| 9,387,015 B2 | 7/2016 | Taylor |
| 9,392,953 B1 | 7/2016 | Gharib |
| 9,393,052 B2 | 7/2016 | Berg et al. |
| 9,402,726 B2 | 8/2016 | Linderman et al. |
| 9,408,615 B2 | 8/2016 | Fitz et al. |
| 9,408,642 B2 | 8/2016 | Wong et al. |
| 9,408,698 B2 | 8/2016 | Miles et al. |
| 9,414,940 B2 | 8/2016 | Stein et al. |
| 9,433,413 B2 | 9/2016 | Montello et al. |
| 9,439,659 B2 | 9/2016 | Schoenefeld et al. |
| 9,439,767 B2 | 9/2016 | Bojarski et al. |
| 9,439,781 B2 | 9/2016 | Gibson |
| 9,445,913 B2 | 9/2016 | Donner et al. |
| 9,452,022 B2 | 9/2016 | McIntosh et al. |
| 9,452,023 B2 | 9/2016 | Boillot et al. |
| 9,452,050 B2 | 9/2016 | Miles et al. |
| 9,452,064 B2 | 9/2016 | Trautwein et al. |
| 9,468,436 B2 | 10/2016 | Groiso |
| 9,468,502 B2 | 10/2016 | Wiebe et al. |
| 9,491,415 B2 | 11/2016 | Deitz et al. |
| 9,492,183 B2 | 11/2016 | Wilkinson et al. |
| 9,493,260 B2 | 11/2016 | Funk et al. |
| 9,495,483 B2 | 11/2016 | Steines et al. |
| 9,495,509 B2 | 11/2016 | Amiot et al. |
| 9,504,502 B2 | 11/2016 | Kuiper et al. |
| 9,510,864 B2 | 12/2016 | Devito |
| 9,517,134 B2 | 12/2016 | Lang |
| 9,517,143 B2 | 12/2016 | Prevost et al. |
| 9,526,514 B2 | 12/2016 | Kelley et al. |
| 9,532,730 B2 | 1/2017 | Wasielewski |
| 9,539,031 B2 | 1/2017 | Fauth |
| 9,539,116 B2 | 1/2017 | Claypool et al. |
| 9,539,760 B2 | 1/2017 | Stahl et al. |
| 9,549,782 B2 | 1/2017 | Park et al. |
| 9,554,411 B1 | 1/2017 | Hall et al. |
| 9,554,910 B2 | 1/2017 | Vanasse et al. |
| 9,561,115 B2 | 2/2017 | Elahinia et al. |
| 9,566,075 B2 | 2/2017 | Carroll |
| 9,579,043 B2 | 2/2017 | Chien et al. |
| 9,585,597 B2 | 3/2017 | McCaullet et al. |
| 9,597,096 B2 | 3/2017 | Aghazadeh |
| 9,597,156 B2 | 3/2017 | Amiot et al. |
| 9,603,613 B2 | 3/2017 | Schoenefeld et al. |
| 9,603,623 B2 | 3/2017 | Brooks et al. |
| 9,603,711 B2 | 3/2017 | Bojarski et al. |
| 9,610,086 B2 | 4/2017 | Park et al. |
| 9,615,834 B2 | 4/2017 | Agmihotri et al. |
| 9,622,712 B2 | 4/2017 | Munro et al. |
| 9,629,723 B2 | 4/2017 | Parisi et al. |
| 9,642,633 B2 | 5/2017 | Frey et al. |
| 9,649,170 B2 | 5/2017 | Park et al. |
| 9,655,729 B2 | 5/2017 | Parisi et al. |
| 9,662,214 B2 | 5/2017 | Li et al. |
| 9,668,748 B2 | 6/2017 | McKinnon et al. |
| 9,668,873 B2 | 6/2017 | Winslow |
| 9,675,471 B2 | 6/2017 | Bojarski et al. |
| 9,693,831 B2 | 7/2017 | Mosnier et al. |
| 9,757,072 B1 | 9/2017 | Urbalejo |
| 9,782,228 B2 | 10/2017 | Mosnier et al. |
| 9,968,408 B1 | 5/2018 | Casey et al. |
| 9,987,048 B2 | 6/2018 | Mosnier et al. |
| 9,993,177 B2 | 6/2018 | Chien et al. |
| 10,045,824 B2 | 8/2018 | Mosnier et al. |
| 2002/0035321 A1 | 3/2002 | Bucholz et al. |
| 2002/0038118 A1 | 3/2002 | Shoham |
| 2002/0045812 A1 | 4/2002 | Ben-Haim et al. |
| 2002/0103432 A1 | 8/2002 | Kawchuk |
| 2003/0191383 A1 | 10/2003 | Ben-Haim et al. |
| 2004/0120781 A1 | 6/2004 | Luca |
| 2004/0143243 A1 | 7/2004 | Wahrburg |
| 2004/0152972 A1 | 8/2004 | Hunter |
| 2004/0167637 A1 | 8/2004 | Biscup |
| 2004/0243148 A1 | 12/2004 | Wasuekewski |
| 2004/0267279 A1 | 12/2004 | Casutt et al. |
| 2005/0149050 A1 | 7/2005 | Stifter et al. |
| 2005/0177239 A1 | 8/2005 | Steinberg |
| 2005/0182320 A1 | 8/2005 | Stifter et al. |
| 2005/0182454 A1 | 8/2005 | Kaula et al. |
| 2005/0203531 A1 | 9/2005 | Lakin et al. |
| 2005/0203532 A1 | 9/2005 | Ferguson et al. |
| 2005/0262911 A1 | 12/2005 | Dankowicz et al. |
| 2006/0015018 A1 | 1/2006 | Jutras et al. |
| 2006/0015030 A1 | 1/2006 | Poulin et al. |
| 2006/0069324 A1 | 3/2006 | Block et al. |
| 2006/0074431 A1 | 4/2006 | Sutton et al. |
| 2006/0136058 A1 | 6/2006 | Pietrzak |
| 2006/0285991 A1 | 12/2006 | McKinley |
| 2006/0287627 A1 | 12/2006 | Johnson |
| 2007/0021682 A1 | 1/2007 | Gharib et al. |
| 2007/0118243 A1 | 5/2007 | Schroeder et al. |
| 2007/0225731 A1 | 9/2007 | Couture et al. |
| 2008/0058945 A1 | 3/2008 | Hajaj et al. |
| 2008/0079546 A1 | 4/2008 | Sensomatic |
| 2008/0108991 A1 | 5/2008 | von Jako |
| 2008/0255575 A1 | 10/2008 | Justis et al. |
| 2009/0024164 A1 | 1/2009 | Neubardt |
| 2009/0194206 A1 | 8/2009 | Jeon et al. |
| 2009/0204159 A1* | 8/2009 | Justis ............... A61B 17/708 606/323 |
| 2009/0254326 A1* | 10/2009 | Isaacs ............... A61B 17/7011 703/11 |
| 2010/0042157 A1 | 2/2010 | Trieu |
| 2010/0100011 A1 | 4/2010 | Roche |
| 2010/0191071 A1 | 7/2010 | Anderson et al. |
| 2010/0217270 A1 | 8/2010 | Polinski et al. |
| 2010/0217336 A1 | 8/2010 | Crawford et al. |
| 2011/0004309 A9 | 3/2011 | Bojarski et al. |
| 2011/0071802 A1 | 3/2011 | Bojarski et al. |
| 2011/0118740 A1 | 5/2011 | Rabiner et al. |
| 2011/0172566 A1 | 7/2011 | Kawchuk |
| 2011/0214279 A1 | 9/2011 | Park et al. |
| 2011/0224796 A1 | 9/2011 | Weiland et al. |
| 2011/0257653 A1 | 10/2011 | Hughes et al. |
| 2011/0257657 A1 | 10/2011 | Turner et al. |
| 2011/0295159 A1 | 12/2011 | Shachar et al. |
| 2011/0306873 A1 | 12/2011 | Shenai et al. |
| 2012/0022357 A1 | 1/2012 | Chang et al. |
| 2012/0035611 A1 | 2/2012 | Kave |
| 2012/0123301 A1 | 5/2012 | Connor et al. |
| 2012/0143090 A1 | 6/2012 | Hay et al. |
| 2012/0172884 A1 | 7/2012 | Zheng et al. |
| 2012/0203289 A1 | 8/2012 | Beerens et al. |
| 2013/0079678 A1 | 3/2013 | Stein et al. |
| 2013/0079679 A1 | 3/2013 | Roche et al. |
| 2013/0079790 A1 | 3/2013 | Stein et al. |
| 2013/0131486 A1 | 5/2013 | Copf et al. |
| 2013/0345718 A1 | 6/2013 | Crawford et al. |
| 2013/0211531 A1 | 8/2013 | Steines et al. |
| 2013/0245631 A1 | 9/2013 | Bettenga |
| 2013/0253599 A1 | 9/2013 | Gorek et al. |
| 2013/0303883 A1 | 11/2013 | Zehavi et al. |
| 2014/0100579 A1 | 4/2014 | Kelman et al. |
| 2014/0135658 A1 | 5/2014 | Hladio et al. |
| 2014/0180415 A1 | 6/2014 | Koss |
| 2014/0194889 A1 | 7/2014 | Chang et al. |
| 2014/0228670 A1 | 8/2014 | Justis et al. |
| 2014/0228860 A1 | 8/2014 | Steines et al. |
| 2014/0244220 A1 | 8/2014 | McKinnon et al. |
| 2014/0257402 A1 | 9/2014 | Barsoum |
| 2014/0272881 A1 | 9/2014 | Barsoum |
| 2014/0296860 A1 | 10/2014 | Stein et al. |
| 2014/0303672 A1 | 10/2014 | Tran et al. |
| 2014/0316468 A1 | 10/2014 | Keiser et al. |
| 2015/0057756 A1 | 2/2015 | Lang et al. |
| 2015/0066145 A1 | 3/2015 | Rogers et al. |
| 2015/0080901 A1 | 3/2015 | Stein |

(56) References Cited

U.S. PATENT DOCUMENTS

| | | | |
|---|---|---|---|
| 2015/0081029 A1 | 3/2015 | Bojarski et al. | |
| 2015/0088030 A1 | 3/2015 | Gharib et al. | |
| 2015/0100066 A1 | 4/2015 | Kostrezewski et al. | |
| 2015/0100091 A1 | 4/2015 | Tohmeh et al. | |
| 2015/0105782 A1 | 4/2015 | D'Lima et al. | |
| 2015/0127055 A1* | 5/2015 | Dvorak | A61B 17/7038 606/279 |
| 2015/0150646 A1 | 6/2015 | Pryor et al. | |
| 2015/0164657 A1 | 6/2015 | Miles et al. | |
| 2015/0182292 A1 | 7/2015 | Hladio et al. | |
| 2015/0223900 A1 | 8/2015 | Wiebe et al. | |
| 2015/0245844 A1 | 9/2015 | Kennedy et al. | |
| 2015/0250597 A1 | 9/2015 | Lang et al. | |
| 2015/0265291 A1 | 9/2015 | Wilkinson | |
| 2015/0305878 A1 | 10/2015 | O'Neil et al. | |
| 2015/0305891 A1 | 10/2015 | Bergin et al. | |
| 2015/0313723 A1 | 11/2015 | Jansen et al. | |
| 2015/0328004 A1 | 11/2015 | Mafhouz | |
| 2015/0366630 A1 | 12/2015 | Gorek et al. | |
| 2016/0000571 A1 | 1/2016 | Mahfouz | |
| 2016/0007983 A1 | 1/2016 | Frey et al. | |
| 2016/0015465 A1 | 1/2016 | Steines et al. | |
| 2016/0022176 A1 | 1/2016 | Le Huec et al. | |
| 2016/0022370 A1 | 1/2016 | Pavlovskaia et al. | |
| 2016/0038161 A1 | 2/2016 | Gibson | |
| 2016/0038238 A1 | 2/2016 | Kostrzewski et al. | |
| 2016/0038242 A1 | 2/2016 | Lo Iacono et al. | |
| 2016/0038293 A1 | 2/2016 | Slamin | |
| 2016/0038307 A1 | 2/2016 | Bettenga | |
| 2016/0045230 A1 | 2/2016 | Lowery et al. | |
| 2016/0045317 A1 | 2/2016 | Lang et al. | |
| 2016/0045326 A1 | 2/2016 | Hansen et al. | |
| 2016/0058320 A1 | 3/2016 | Chien et al. | |
| 2016/0058523 A1 | 3/2016 | Chien et al. | |
| 2016/0074052 A1 | 3/2016 | Keppler et al. | |
| 2016/0074202 A1 | 3/2016 | Reed et al. | |
| 2016/0081754 A1 | 3/2016 | Kostrzewski et al. | |
| 2016/0095710 A1 | 4/2016 | Juszczyk et al. | |
| 2016/0100907 A1 | 4/2016 | Gomes | |
| 2016/0106483 A1 | 4/2016 | Mayer et al. | |
| 2016/0128847 A1 | 5/2016 | Kurtaliaj et al. | |
| 2016/0143744 A1 | 5/2016 | Bojarski et al. | |
| 2016/0157751 A1 | 6/2016 | Mahfouz | |
| 2016/0199101 A1 | 7/2016 | Sharifi-Mehr et al. | |
| 2016/0210374 A1 | 7/2016 | Mosnier et al. | |
| 2016/0228192 A1 | 8/2016 | Jansen et al. | |
| 2016/0235480 A1 | 8/2016 | Scholl et al. | |
| 2016/0235493 A1 | 8/2016 | LeBoeuf, II et al. | |
| 2016/0242857 A1 | 8/2016 | Scholl | |
| 2016/0242934 A1 | 8/2016 | Van der Walt et al. | |
| 2016/0256279 A1 | 9/2016 | Sanders et al. | |
| 2016/0256285 A1 | 9/2016 | Jansen | |
| 2016/0262800 A1 | 9/2016 | Scholl et al. | |
| 2016/0262895 A1 | 9/2016 | Shea et al. | |
| 2016/0270802 A1 | 9/2016 | Fang et al. | |
| 2016/0270931 A1 | 9/2016 | Trieu | |
| 2016/0274571 A1 | 9/2016 | LaVallee et al. | |
| 2016/0283676 A1 | 9/2016 | Kelly et al. | |
| 2016/0287395 A1 | 10/2016 | Khalili et al. | |
| 2016/0296285 A1 | 10/2016 | Chaoui et al. | |
| 2016/0310221 A1 | 10/2016 | Bar et al. | |
| 2016/0331417 A1 | 11/2016 | Trautwein et al. | |
| 2016/0354009 A1 | 12/2016 | Schroeder | |
| 2016/0354161 A1 | 12/2016 | Deitz | |
| 2016/0360997 A1 | 12/2016 | Yadav et al. | |
| 2017/0000568 A1 | 1/2017 | O'Neil et al. | |
| 2017/0007145 A1 | 1/2017 | Gharib et al. | |
| 2017/0007328 A1 | 1/2017 | Cattin et al. | |
| 2017/0007408 A1 | 1/2017 | Fitz et al. | |
| 2017/0027590 A1 | 2/2017 | Amiot et al. | |
| 2017/0027617 A1 | 2/2017 | Strnad | |
| 2017/0035580 A1 | 2/2017 | Murphy | |
| 2017/0056179 A1 | 3/2017 | Lorio | |
| 2017/0056196 A1 | 3/2017 | Kuiper et al. | |
| 2017/0071503 A1 | 3/2017 | Wasiewlewski | |
| 2017/0119472 A1 | 5/2017 | Herrmann et al. | |
| 2017/0132389 A1 | 5/2017 | McCaulley et al. | |
| 2017/0135706 A1 | 5/2017 | Frey et al. | |
| 2017/0135707 A9 | 5/2017 | Frey et al. | |
| 2017/0143426 A1 | 5/2017 | Isaacs et al. | |
| 2017/0143494 A1 | 5/2017 | Mahfouz | |
| 2017/0143502 A1 | 5/2017 | Yadin et al. | |
| 2017/0156798 A1 | 6/2017 | Wasielewski | |
| 2017/0189121 A1 | 7/2017 | Frasier et al. | |
| 2017/0245937 A1 | 8/2017 | Mosnier | |
| 2017/0252107 A1 | 9/2017 | Turner et al. | |
| 2018/0132942 A1 | 5/2018 | Mosnier et al. | |
| 2018/0256067 A1 | 9/2018 | Chen et al. | |
| 2018/0289396 A1 | 10/2018 | McGahan et al. | |
| 2018/0295584 A1 | 10/2018 | Gliner et al. | |
| 2018/0303552 A1 | 10/2018 | Ryan et al. | |
| 2019/0069956 A1 | 3/2019 | Ryan et al. | |

FOREIGN PATENT DOCUMENTS

| | | |
|---|---|---|
| CN | 1816134 | 8/2006 |
| CN | 102805677 | 12/2012 |
| CN | 104127229 | 11/2014 |
| CN | 205073000 | 3/2016 |
| CN | 103892953 | 5/2016 |
| CN | 104434287 | 1/2017 |
| CN | 104323843 | 7/2017 |
| CN | 105078555 | 11/2018 |
| EP | 1570781 | 7/2005 |
| EP | 2053580 | 4/2009 |
| EP | 2749235 | 7/2014 |
| EP | 2754419 | 7/2014 |
| EP | 2496183 | 9/2015 |
| EP | 3000443 | 3/2016 |
| EP | 2608749 | 8/2016 |
| EP | 2403434 | 4/2017 |
| EP | 3431032 | 1/2019 |
| FR | 1358988 | 4/1964 |
| FR | 1360208 | 5/1964 |
| IL | 248660 | 2/2017 |
| IL | 249833 | 3/2017 |
| JP | 2016-537036 | 12/2016 |
| JP | 2016-540610 | 12/2016 |
| SU | 1497721 | 7/1979 |
| SU | 1704102 | 1/1992 |
| WO | WO1998/55038 | 12/1998 |
| WO | WO 200053077 | 9/2000 |
| WO | WO2004/017836 | 3/2004 |
| WO | WO 2004/089224 | 10/2004 |
| WO | WO 2005/074368 | 8/2005 |
| WO | WO 2006/075331 | 7/2006 |
| WO | WO 2006/084193 | 8/2006 |
| WO | WO 2007/035925 | 3/2007 |
| WO | WO 2007/038290 | 4/2007 |
| WO | WO 2008/002588 | 1/2008 |
| WO | WO2008/079546 | 7/2008 |
| WO | WO 2008/124079 | 10/2008 |
| WO | WO2009119181 | 10/2009 |
| WO | WO 2010/044880 | 4/2010 |
| WO | WO 2010/064234 | 6/2010 |
| WO | WO2010/121147 | 10/2010 |
| WO | WO 2010/147972 | 12/2010 |
| WO | WO 2011/021192 | 2/2011 |
| WO | WO2012/012863 | 2/2012 |
| WO | WO 2012/131660 | 10/2012 |
| WO | WO2013/003435 | 1/2013 |
| WO | WO2016102026 | 12/2014 |
| WO | WO2015/040552 | 3/2015 |
| WO | WO2015/056131 | 4/2015 |
| WO | WO2015/079011 | 6/2015 |
| WO | WO2015/89118 | 6/2015 |
| WO | WO2015185219 | 6/2015 |
| WO | WO2016044352 | 9/2015 |
| WO | WO 2015/195843 | 12/2015 |
| WO | WO2015/200720 | 12/2015 |
| WO | WO2016088130 | 12/2015 |
| WO | WO2016/019424 | 2/2016 |
| WO | WO2016/019425 | 2/2016 |
| WO | WO2016/019426 | 2/2016 |

(56) References Cited

FOREIGN PATENT DOCUMENTS

| WO | WO2016/26053 | 2/2016 |
|---|---|---|
| WO | WO2016/032875 | 3/2016 |
| WO | WO2016/048800 | 3/2016 |
| WO | WO 2016/012726 | 4/2016 |
| WO | WO2016/094826 | 6/2016 |
| WO | WO2017001851 | 6/2016 |
| WO | WO2016/137347 | 9/2016 |
| WO | WO2016/148675 | 9/2016 |
| WO | WO2016/165030 | 10/2016 |
| WO | WO2017/39596 | 3/2017 |
| WO | WO 2017/064719 | 4/2017 |
| WO | WO 2017/066518 | 4/2017 |
| WO | WO2017/077356 | 5/2017 |
| WO | WO2017/079655 | 5/2017 |
| WO | WO 2017/127838 | 7/2017 |
| WO | WO 2017/221257 | 12/2017 |
| WO | WO 2018/087758 | 5/2018 |
| WO | WO2018/131044 | 7/2018 |
| WO | WO2018/185755 | 10/2018 |
| WO | WO 2018/193316 | 10/2018 |
| WO | WO 2018/193317 | 10/2018 |
| WO | WO2019144452 | 1/2019 |

OTHER PUBLICATIONS

International Search Report in PCT Application PCT/IB2014/064586, dated Dec. 23, 2014, in 2 pages.

International Search Report in PCT Application PCT/US2016/060676, dated Nov. 5, 2017 in 7 pages.

Abe et al. "Scoliosis corrective force estimation from the implanted rod deformation using 3 D FEM analysis", 2015, Scoliosis 10(Suppl 2):52, 6 pages.

Aubin et al. "Preoperative Planning Simulator for Spinal Deformity Surgeries", Spine 2008, 33(20):2143-2152.

Reinshagen et al. "A novel minimally invasive technique for lumbar decompression, realignment, and navigated interbody fusion", J Clin Neurosci. 2015, 22(9):1484-1490; XP055503028.

International Search Report and Written Opinion in PCT Application PCT/IB2014/065150, dated Oct. 8, 2014 in 9 pages.

Rickert et Al., "Posterior lumbar interbody fusion implants", Orthopaede, Springer Verlag, Berlin, DE vol. 44, No. 2 dated Jan. 28, 2015 pp. 162-169.

Spontech Medical AG Vertaplan—die Software für Wirbelsäulenchirurgen, Aug. 29, 2013 Retrieved from the Internet: URL: https://www.youtube.com/watch?v=q0qhW1T1cp8 in 1 page.

\* cited by examiner

METHODS, SYSTEMS, AND DEVICES FOR DESIGNING AND MANUFACTURING A SPINAL ROD

CROSS-REFERENCE TO RELATED APPLICATIONS

This application is a continuation of U.S. patent application Ser. No. 15/694,227, filed on Sep. 1, 2017, and titled METHODS, SYSTEMS, AND DEVICES FOR DESIGNING AND MANUFACTURING A ROD TO SUPPORT A VERTEBRAL COLUMN OF A PATIENT, which is a continuation of U.S. patent application Ser. No. 15/469,302, filed on Mar. 24, 2017, and titled METHODS, SYSTEMS, AND DEVICES FOR DESIGNING AND MANUFACTURING A ROD TO SUPPORT A PATIENT'S VERTEBRAL COLUMN, which is a continuation of U.S. patent application Ser. No. 15/024,150, filed on Mar. 23, 2016, and titled METHOD MAKING IT POSSIBLE TO PRODUCE THE IDEAL CURVATURE OF A ROD OF VERTEBRAL OSTEOSYNTHESIS MATERIAL DESIGNED TO SUPPORT A PATIENT VERTEBRAL COLUMN, which is a U.S. national stage entry of PCT Application No. PCT/IB2014/065150, filed Oct. 8, 2014, and titled METHOD MAKING IT POSSIBLE TO ACHIEVE THE IDEAL CURVATURE OF A ROD FOR VERTEBRAL OSTEOSYNTHESIS EQUIPMENT DESIGNED TO SUPPORT A PATIENT'S VERTEBRAL COLUMN, which claims priority to and the benefit of French Patent Application No. 1360208, filed Oct. 18, 2013, and titled PROCEDE PERMETTANT DE REALISER LA COURBURE IDEALE D'UNE TIGE D'UN MATERIEL D'OSTEOSYNTHESE VERTEBRALE DESTINEE A ETAYER LA COLONNE VERTEBRALE D'UN PATIENT. The entire contents of each of the above-identified patent applications are incorporated by reference herein and made a part of this specification. Any and all priority claims identified in the Application Data Sheet, or any correction thereto, are hereby incorporated by references under 37 CFR 1.57.

FIELD OF THE INVENTION

The present invention relates to a method making it possible to produce the ideal curvature of a rod for vertebral osteosynthesis equipment designed to correct a patient's vertebral column.

BACKGROUND OF THE INVENTION

It is known to analyze a patient's vertebral column in reference to so called "pelvic" parameters that are documented in the scientific literature. The appended FIG. 1 very diagrammatically shows the base of a vertebral column, i.e., a part of the lumbar vertebrae L and the sacrum S, as well as the femoral heads TF; said pelvic criteria are:

the SS (sacral slope) criterion, which is the incline angle of the plate of S1 (first vertebra of the sacrum), relative to the horizontal;

the PV (pelvic version) criterion, which is the angle formed by the straight segment connecting the center of the femoral heads TF and the center of the plate of S1 with the vertical;

the PI (pelvic incidence) criterion, which is the angle formed by the straight segment connecting the center of the femoral heads TF and the center of the plate of S1 with the perpendicular to the plate of S1.

It is accepted that an individual will adopt a natural vertebral column posture, called "economic", avoiding pain and other pathologies, if his pelvic parameters in particular are in agreement with his back morphotype. If this is not the case, surgical treatment may be considered in order to reestablish proper posture of the vertebral column, in which that agreement exists.

It is well known to perform this type of recovery using rigid vertebral rods, in particular metal, fastened to the vertebrae using pedicle screws, which must be curved suitably based on the correction to be done. The publication of patent application No. WO 98/55038 illustrates an equipment of this type.

It has been shown that imparting the appropriate curvature to a straight rod may be very difficult for a surgeon, the curvature being more or less pronounced in any given location of the rod. Currently, such a curvature is done at the surgeon's discretion and a call greatly on the latter's experience and dexterity. The trial and error necessary to obtain an appropriate curvature have the significant drawback of extending the operation time, which is not desirable for the patient, and the risk of implanting a rod with a non-ideal curvature cannot be ruled out.

OBJECTS OF THE INVENTION

The present invention aims to resolve this essential drawback.

Patent application publications Nos. WO 2004/017836 A2, US 2009/254326 A1 and WO 2008/079546 A2 describe methods not making it possible to achieve the same in a satisfactory manner.

SUMMARY OF THE INVENTION

To achieve that aim, the method according to the invention comprises the following steps:

a) taking a sagittal preoperative x-ray of the vertebral column of the patient to be treated, extending from the cervical vertebrae to the femoral heads;

b) on that x-ray, identifying:

the points and straight segments making it possible to calculate the so-called "pelvic" parameters, i.e., the sacral slope, the pelvic version and the pelvic incidence, the center of the plate of the first vertebra of the sacrum, called S1;

the center of the second vertebra of the sacrum, called S2;

the center of the lower plate of a reference dorsal vertebra, in particular the twelfth dorsal vertebra, called T12;

the center of the lower plate of a reference cervical vertebra, in particular the seventh cervical vertebra, called C7;

c) depicting, on the x-ray, a first curved segment beginning at the center of the plate of S1, tangent to the segment going from the center of S2 to the center of the plate of S1, passing through the centers of the bodies of the vertebrae of segment L5-L1 and ending at the center of the lower plate of said reference dorsal vertebra;

d) depicting, on the x-ray, a second curved segment tangent to the first curved segment at the center of the lower plate of said reference dorsal vertebra, passing through the centers of the bodies of the vertebrae of the segment extending between said reference dorsal vertebra and said reference cervical vertebra and going to the center of the lower plate of said reference cervical vertebra;

e) identifying, on that x-ray, the correction(s) to be made to the vertebral column;

f) pivoting portions of said x-ray relative to other portions of that x-ray, based on the corrections to be made, so as to show the correction(s) to be made to the vertebral column;

g) recalculating said first and second curved segments based on the correction(s) made in step f) and depicting those curved segments on said x-ray;

h) determining the length of the vertebral segment to be corrected, therefore the length of each vertebral rod to be implanted;

i) for each vertebra of that segment,
either reading, on said x-ray, the distance from the center of the body of the vertebra to the posterior face of the pedicle of that vertebra, i.e., the entry face of a pedicle screw in that pedicle; or
reading that same distance in a previously established databank, containing, for each vertebra, the mean value, established statistically, of that distance for the type of patient in question, in particular based on the age, gender and size of that patient;

j) performing, on said x-ray, a displacement of the sagittal curvature segment determined in step g), extending over the vertebral segment to be corrected determined in step h), over the distances read in step i) for the vertebrae in question, and recalculating the curvature of that segment in the displacement position;

k) from a straight vertebral rod, producing the curvature of that rod according to the shape of said sagittal curvature segment in said displacement position, recalculated in step j).

The method according to the invention thereby makes it possible to impart the appropriate curvature to a straight rod easily, that rod being fully suitable for the correction to be done.

Preferably, the method also comprises the following steps:

taking a frontal x-ray of the vertebral column of the patient to be treated;

on that x-ray, identifying one or more potential portions of the vertebral column that are curved in the frontal plane, and, for each of those curved portions to be straightened, defining a reference point at the vertebra on which the curved portion begins and a reference point at the vertebra on which the curved portion ends;

for each of these curved portions, measuring the length of the segment extending between the reference points identified on that curved portion;

identifying, on the aforementioned sagittal x-ray, these same reference points on these same vertebrae, and identifying the corresponding points on said sagittal curvature segment; and performing homothetic stretching of the portion of said sagittal curvature segment extending between these corresponding points, so as to give that portion a length identical to that existing between said reference points and to thereby obtain a recalculated sagittal curvature segment, taking into account the elongation of the vertebral column resulting from the correction of that column in the frontal plane.

Preferably, the identification in step e) of the correction(s) to be done includes either the identification of posterior osteotomies to be done on the plates of one or more lumbar vertebrae in order to obtain a corrected lumbar curvature, or the determination of the shape of one or more vertebral implants to be inserted into the intervertebral spaces of those vertebrae to obtain that same corrected lumbar curvature, in particular the determination of the angulation of the wedge shape those implants must have.

Preferably, the method comprises, after step j), the transfer of data relative to the rod to be produced to a service provider responsible for producing the curvature of the rod.

Thus, a practitioner, having determined the shape of the rod to be implanted using the method according to the invention, transfers the data relative to the rod to be produced to a service provider responsible for producing the curvature of the rod. Once that curvature is produced, the service provider will deliver the curved rod to the practitioner, who will be able to operate on the patient with his vertebral rod that is ready to be implanted.

The invention will be well understood, and other features and advantages thereof will appear, in reference to the appended diagrammatic drawing, showing, as a non-limiting example, different steps of the method in question.

DESCRIPTION OF THE PREFERRED EMBODIMENTS

Figure 1:
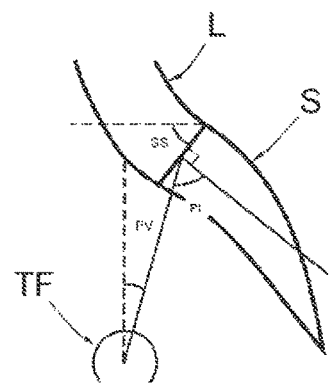
FIG. 1 is a diagrammatically view of the base of a vertebral column.
Figure 2:
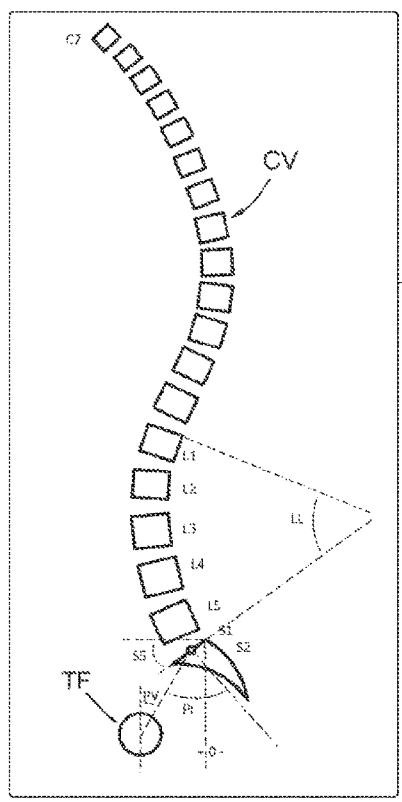
FIG. 2 is a very diagrammatic view of a vertebral column CV as shown on an x-ray, referencing the lumbar lordosis LL, the names of the vertebrae S2-L5 in question, the femoral heads TF, a point situated at the center of the plate of S1, and the pelvic criteria SS, PV, PI explained above in reference to FIG. 1.

FIGS. 2 to 11 illustrate a method making it possible to produce the ideal curvature of a vertebral rod TV that is a part of a vertebral osteosynthesis equipment, designed to correct a patient's vertebral column by performing a correction of that vertebral column. This method comprises the following successive steps:

FIG. 2: taking a sagittal preoperative x-ray RS of the vertebral column of the patient to be treated, extending from the cervical vertebrae to the femoral heads, and identifying, on that x-ray RS:

LL: the vertebral segment to be treated;

L1, L2, L3, L4, L5, S1, S2, T12, C7: the first, second, third, fourth and fifth lumbar vertebrae, the first and second vertebrae of the sacrum, the twelfth dorsal vertebra and the seventh cervical vertebra, respectively;

SS, PV, PI: the aforementioned pelvic criteria;

TF: the femoral heads, shown by a circle in the figure;

also identifying, by a dot, the center of the plate of S1.

Figure 3:
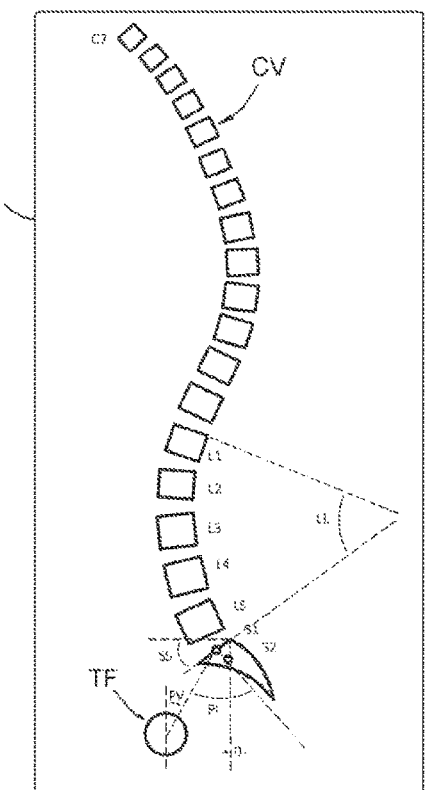
FIG. 3 is a view similar to FIG. 2, in which the center point of the second vertebra of the sacrum, called S2, is shown.

FIG. 3: identifying, on the x-ray RS, the center of the plate of S2 using a dot.

Figure 4:
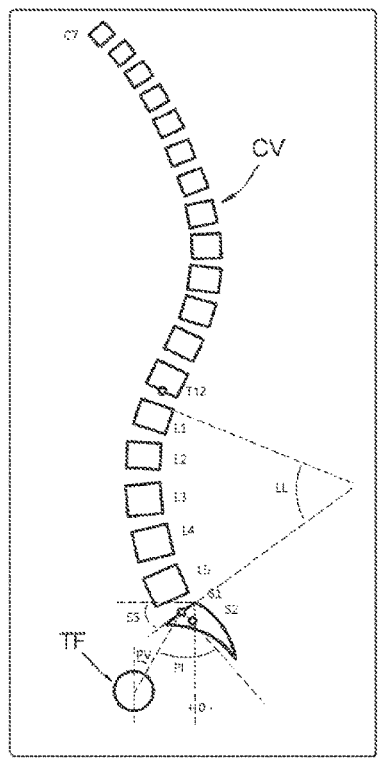
FIG. 4 is a view similar to FIG. 3, in which the center point of the lower plate of the twelfth dorsal vertebra, called T12, is shown.

FIG. 4: identifying, on the x-ray RS, the center of the lower plate of T12 using a dot.

Figure 5:
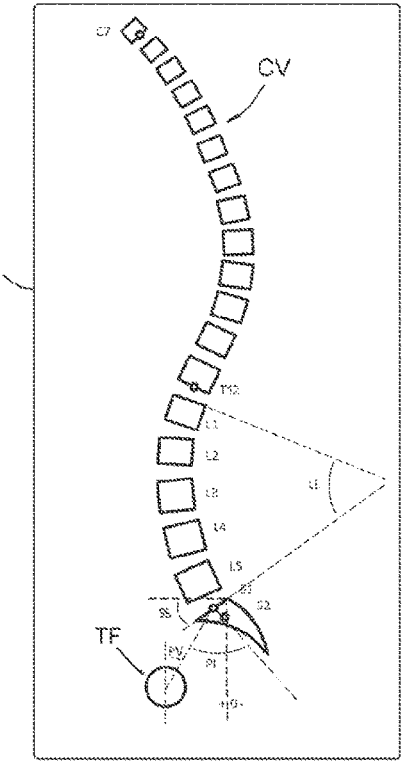
FIG. 5 is a view similar to FIG. 4, in which the center point of the lower plate of the seventh cervical vertebra, called C7, is shown.

FIG. 5: identifying, on the x-ray RS, the center of the lower plate of C7 using a dot.

Figure 6:
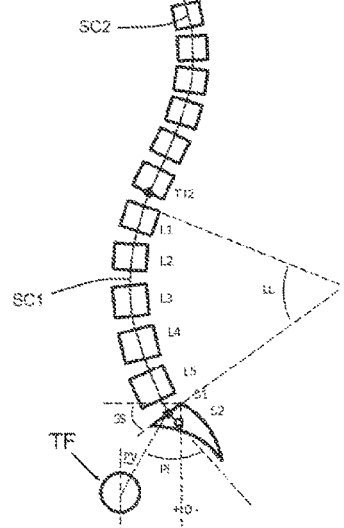
FIG. 6 is a view similar to FIG. 5, in which a first curved segment SC1 and a second curved segment SC2 are further shown.

FIG. 6: depicting, on said x-ray RS, said first and second curved segments SC1, SC2; the first curved segment SC1 begins at the center of the plate of S1, tangent to the segment going from the center of S2 to the center of the plate of S1, passes through the centers of the bodies of the vertebrae of segment L5-L1 and ends at the center of the lower plate of T12; the second curved segment SC2 is tangent to the first curved segment SC1 at the center of the lower plate of T12, passes through the centers of the bodies of the vertebrae of segment T11-C6 and goes to the center of the lower plate of C7.

Figure 7:
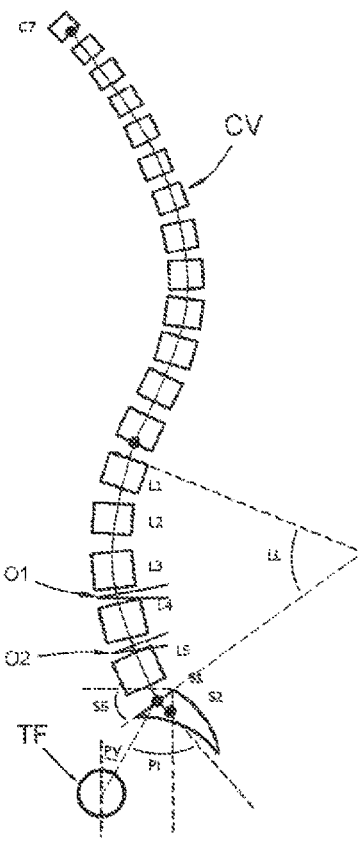
FIG. 7 is a view similar to FIG. 6, in which osteotomies O1, O2 to be done on the upper plates, posterior sides, of vertebrae L4 and L5 (fourth and fifth lumbar vertebra) are also shown.

FIG. 7: identifying, on the x-ray RS, the correction(s) of the vertebral column that must be performed, and in particular identifying the osteotomies O1, O2 to be done in order to obtain a corrected lumbar curvature; in the illustrated example, the determination is made to perform an osteotomy O1 of 10.degree. on the upper plate of L4 and an osteotomy O2 of 10.degree. on the upper plate of L5.

Figure 8:
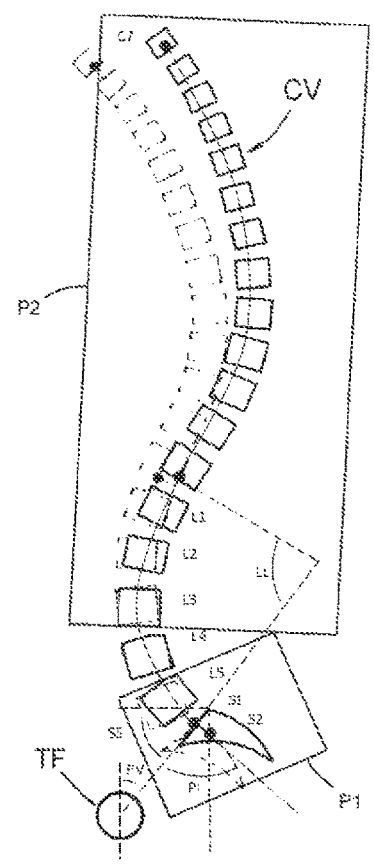
FIG. 8 is a view similar to FIG. 7, showing two portions P1, P2 of the x-ray, delimited by frames, that have been pivoted relative to the respective positions that those same portions occupy in FIG. 7, in the counterclockwise direction regarding P1 and the clockwise direction regarding P2; these new positions are corrected positions of the vertebral column CV, made possible by the corrected lumbar curvature made possible by the osteotomies O1, O2 to be done; in order to view the correction made, the uncorrected vertebral column, as shown in FIG. 7, is superimposed on the corrected vertebral column shown by FIG. 8, that uncorrected vertebral column being shown in thin and broken lines.

FIG. 8: pivoting the portions P1 and P2 of the x-ray RS relative to the rest of that x-ray RS, based on the osteotomies O1, O2 to be done; in the illustrated example, the portion P1 pivots by 10.degree. in the counterclockwise direction relative to the portion of the x-ray on which L4 is located (angulation made possible by the osteotomy O2) and the portion P2 pivots by 10.degree. in the clockwise direction relative to the portion of the x-ray on which L4 is located (angulation made possible by the osteotomy O1). Said first and second curved segments SC1 and SC2 are then recalculated based on the correction(s) made and are shown on the x-ray RS.

Figure 9:
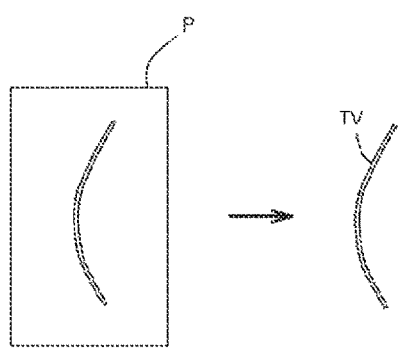
FIG. 9 is a view similar to FIG. 8, showing, in broken lines, the respective distances DL5 to DT12 which, for each of vertebrae L5 to T12, go from the center of the body of the vertebra to the posterior face of a pedicle of that vertebra.
Figure 10:
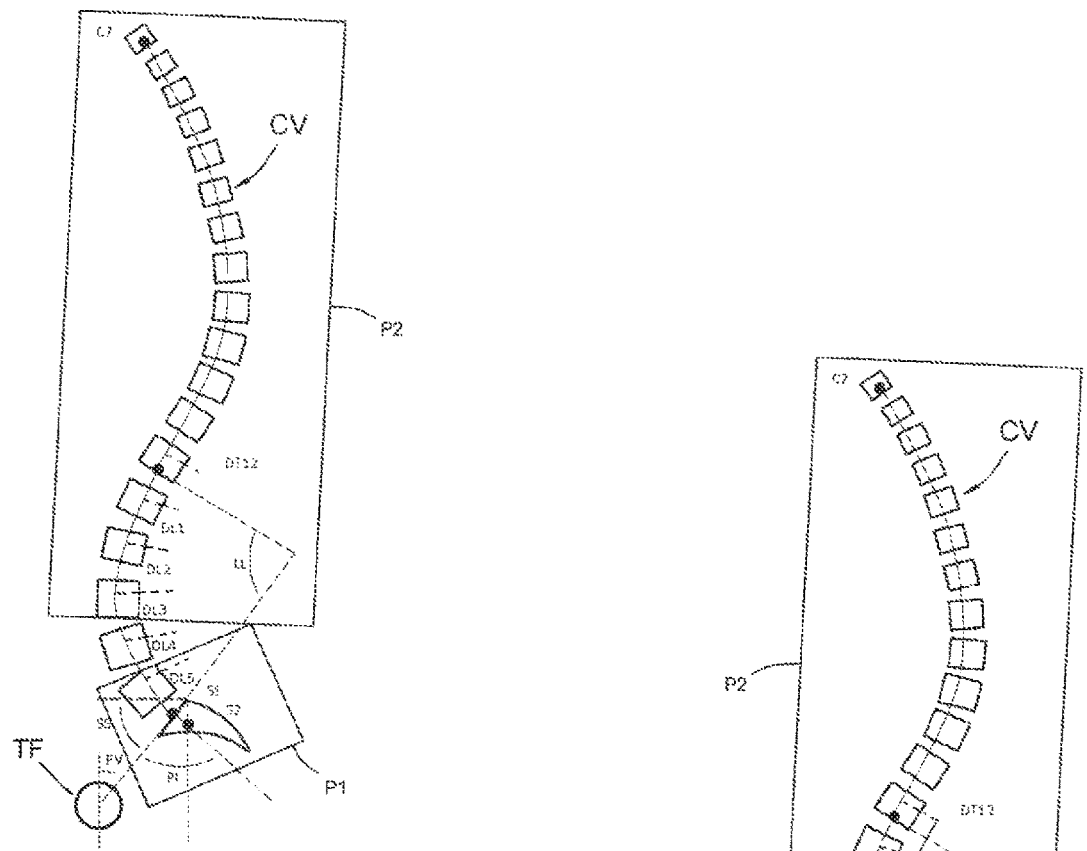
FIG. 10 is a view similar to FIG. 9, showing a sagittal curvature segment SC that corresponds to the curvature to be given to a vertebral rod to produce the desired correction of the vertebral column.

FIG. 9: the length of the vertebral segment to be corrected is determined (in the case at hand, L5-T12), which makes it possible to determine the length of each vertebral rod TV to be implanted; for each vertebra of that segment, the respective distances DL5 to DT12 are determined from the center of the body of the vertebrae to the posterior face of a pedicle of that vertebra, i.e., the entry face of a pedicle screw in the pedicle; these distances are either read on the x-ray RS, or are read in a previously established databank, containing, for each vertebra, the mean value, established statistically, of that distance for the type of patient in question, in particular based on the age, gender and size of that patient;

FIG. 10: a displacement of the curved segment is then done, on the x-ray RS, over the respective distances DL5 to DT12, and the curvature of that segment is recalculated in the displacement position.

Figure 11:
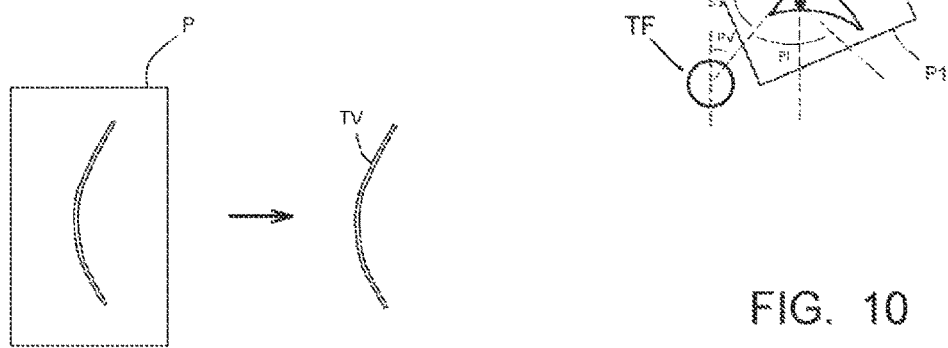
FIG. 11 is, on the left side of that figure, a view of a plane of the curved vertebral rod to be obtained, established from said sagittal curvature segment SC, and, on the right side of that figure, a view of the curved vertebral rod TV, obtained from that plane P.

FIG. 11: after the diameter of the vertebral rod TV to be used has been determined based on the patient in question, a plane P of the curvature of that rod is established, from which the rod TV is made, by curvature from a straight vertebral rod, in particular by cold bending.

Figures 12, 13:
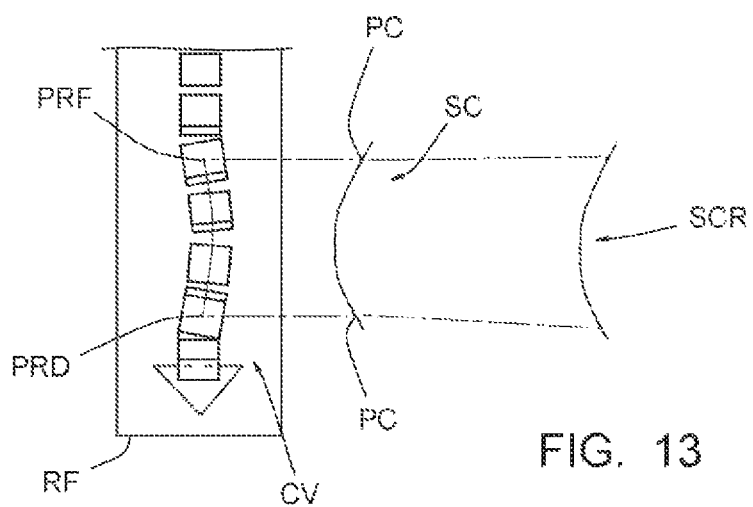
FIG. 12 is, on the left, a partial view of a frontal x-ray RF of the vertebral column of the patient to be treated, and, on the right, a side view of said sagittal curvature segment SC, on which reference points PC are identified.
FIG. 13 is a view of a recalculated sagittal curvature segment SCR, obtained following stretching of a portion of the sagittal curvature segment SC.

FIGS. 12 and 13 show the following steps that the method may comprise:

FIG. 12:

also taking a frontal x-ray RF of the vertebral column CV of the patient to be treated;

on that x-ray RF, identifying one or more potential portions of that vertebral column CV that are curved in the frontal plane, and which must therefore be corrected, and a reference point PRD at the center of the body of the vertebra on which the curved portion begins and a reference point PRF at the center of the body of the vertebra on which the curved portion ends;

measuring the length of the curved segment extending between those reference points PRD, PRF;

identifying, on the aforementioned sagittal x-ray RS, these same reference points PRD, PRF on these same vertebrae, and identifying the corresponding points PC on said sagittal curvature segment SC; and performing homothetic stretching of the portion of said sagittal curvature segment SC extending between these corresponding points PC, so as to give that portion a length identical to that separating the aforementioned reference points PRD, PRF.

FIG. 13: a recalculated sagittal curvature segment SCR is thus obtained, taking the elongation of the vertebral column resulting from the correction of that column in the frontal plane into account.

The method according to the invention thus has the decisive advantage of making it possible to produce the ideal curvature of a rod for vertebral osteosynthesis equipment designed to correct a patient's vertebral column.

What is claimed is:

1. A system for manufacturing a patient-specific implantable spinal rod to correct a vertebral column of a patient, the system comprising:

an interface for analyzing one or more preoperative images of a patient of the vertebral column, wherein the one or more preoperative images of the patient is analyzed by:

identifying one or more corrections to be made to the vertebral column;

generating one or more modified preoperative images by modifying the one or more preoperative images of the patient by:

correcting a first portion of the one or more preoperative images of the patient relative to a reference portion of the one or more preoperative images, wherein the first portion of the one or more preoperative images comprises sacral vertebrae of the vertebral column; and correcting a second portion of the one or more preoperative images of the patient relative to the reference portion of the one or more preoperative images, wherein the second portion of the one or more preoperative images comprises cervical vertebrae of the vertebral column;

determining a first curved segment of the vertebral column on the one or more modified preoperative images generated based on the corrected first portion and the second portion, wherein the first curved segment comprises a portion of the vertebral column below the reference portion;

determining a second curved segment of the vertebral column on the one or more modified preoperative images, wherein the second curved segment comprises a portion of the vertebral column above the reference portion, wherein the second curved segment comprises a different curvature than the first curved segment;

preoperatively calculating a degree of angular correction to obtain a corrected curvature of the vertebral column of the patient, the preoperatively calculated degree of angular correction based at least in part on one or more of a curvature of the first curved segment or a curvature of the second curved segment; and the interface further configured to generate preoperative data instructions based at least in part on the preoperatively calculated degree of angular correction and the corrected curvature of the vertebral column of the patient, the generated preoperative data instructions configured for use by a manufacturing apparatus to manufacture the customized implantable spinal rod, wherein the interface comprises a computer processor and an electronic storage medium.

2. The system of claim 1, wherein the reference portion comprises L4.

3. The system of claim 1, wherein the first curved segment passes through one or more of vertebrae L1 to L5.

4. The system of claim 1, wherein the first curved segment is between a first vertebra of a sacrum and a lower plate of a reference dorsal vertebra.

5. The system of claim 4, wherein the reference dorsal vertebra is a twelfth dorsal vertebra.

6. The system of claim 4, wherein the first curved segment is tangent to a straight line from a center of a second vertebra of the sacrum to a center of the first vertebrae of the sacrum.

7. The system of claim 1, wherein the second curved segment passes through one or more of vertebrae C6 to T11.

8. The system of claim 1, wherein the interface is further configured to determine a length of the customized implantable spinal rod.

9. The system of claim 8, wherein the length of the customized implantable spinal rod is determined by obtaining the length from a database containing, for each vertebra of a vertebral segment to be corrected, a reference value for a type of patient based on one or more of age, gender, or size.

10. The system of claim 1, wherein the one or more preoperative images of the patient comprises one or more sagittal x-ray images.

11. The system of claim 1, wherein the one or more preoperative images of the patient comprises one or more sagittal x-ray images and one or more frontal x-ray images.

12. The system of claim 11, wherein the interface is further configured to analyze the one or more frontal preoperative x-ray images of the vertebral column of the patient, wherein the one or more frontal preoperative x-ray images is analyzed by:

identifying one or more portions of the vertebral column that is curved in a frontal plane;

for each of the one or more portions, defining a first frontal reference point in the vertebra at which a frontal curvature begins and a second frontal reference point in the vertebra at which the frontal curvature ends;

for each of the one or more portions, determining a length extending between the first frontal reference point and the second frontal reference point; and identifying, on the one or more sagittal preoperative x-ray images, the first frontal reference point and the second frontal reference point for each of the one or more portions and identifying a first corresponding sagittal reference point and a second corresponding sagittal reference point.

13. The system of claim 1, wherein the identifying the one or more corrections to be made to the vertebral column comprises identifying one or more posterior osteotomies to be performed on one or more plates of a lumbar vertebrae to obtain a corrected lumbar curvature.

14. The system of claim 1, wherein the identifying the one or more corrections to be made to the vertebral column comprises determining a shape of one or more vertebral implants to be inserted into one or more intervertebral spaces of a lumbar vertebrae to obtain a corrected lumbar curvature.

15. The system of claim 14, wherein the determined shape of the one or more vertebral implants comprises an angulation of a wedge shape of the one or more vertebral implants.

16. The system of claim 1, wherein the identifying the one or more corrections to be made to the vertebral column comprises identifying one or more posterior osteotomies to be performed on one or more plates of a lumbar vertebrae to obtain a corrected lumbar curvature.

17. The system of claim 1, wherein the identifying the one or more corrections to be made to the vertebral column comprises determining a shape of one or more vertebral implants to be inserted into one or more intervertebral spaces of a lumbar vertebrae to obtain a corrected lumbar curvature.

18. The system of claim 1, wherein the interface is further configured to transmit the generated preoperative data instructions to the manufacturing apparatus to manufacture the customized implantable spinal rod.

19. The system of claim 1, wherein the one or more corrections to be made to the vertebral column are identified by performing one or more osteotomies.

20. The system of claim 19, wherein the one or more osteotomies are performed on one or more of an upper plate of L4 and an upper plate of L5.

* * * * *

UNITED STATES PATENT AND TRADEMARK OFFICE
CERTIFICATE OF CORRECTION

PATENT NO.      : 10,314,657 B2
APPLICATION NO. : 16/038694
DATED           : June 11, 2019
INVENTOR(S)     : Thomas Mosnier et al.

Page 1 of 1

It is certified that error appears in the above-identified patent and that said Letters Patent is hereby corrected as shown below:

On the Title Page

Item (63), below "(Continued)" insert item (30), --Foreign Application Priority Data
Oct. 18, 2013 (FR) ................ 1360208--, as a new item entry.

Page 2, item (56), Line 8, under U.S. Patent Documents, change "5,514,130" to --5,514,180--.

Page 2, item (56), Line 22, under U.S. Patent Documents, change "6,736,930" to --6,786,930--.

Page 3, item (56), Line 32, under U.S. Patent Documents, change "9,493,260" to --9,498,260--.

In the Specification

Column 1, Line 64, change "P1" to --PI--.

Column 6, Line 10, change "patient;" to --patient.--.

Signed and Sealed this
First Day of October, 2019

Andrei Iancu
*Director of the United States Patent and Trademark Office*